United States Patent [19]

Berentey et al.

[11] Patent Number: 4,651,724
[45] Date of Patent: Mar. 24, 1987

[54] BONE JOINING PLATE

[75] Inventors: György Berentey, Budapest; András Sárváry, Vecses; József Feczkó, Budapest; Pál Pásztor, Nagykáta, all of Hungary

[73] Assignee: Technomed Gmk, Hodmezovasarhely, Hungary

[21] Appl. No.: 874,802

[22] Filed: Jun. 13, 1986

Related U.S. Application Data

[63] Continuation of Ser. No. 610,639, May 16, 1984, abandoned.

[51] Int. Cl.$^4$ ............................................. A61F 5/04
[52] U.S. Cl. ............................................. 128/92 YP
[58] Field of Search ..................... 128/92 YP, 92 YM

[56] References Cited

U.S. PATENT DOCUMENTS

| | | | |
|---|---|---|---|
| 3,824,995 | 7/1974 | Getscher et al. | 128/92 D |
| 4,120,298 | 10/1978 | Fixel | 128/92 D |
| 4,269,180 | 5/1981 | Dall et al. | 128/92 D |
| 4,364,382 | 12/1982 | Mennen | 128/92 D |
| 4,473,068 | 9/1984 | Oh | 128/92 D |
| 4,488,543 | 12/1984 | Tornier | 128/92 D |

Primary Examiner—Gene Mancene
Assistant Examiner—C. W. Shedd
Attorney, Agent, or Firm—Mandeville and Schweitzer

[57] ABSTRACT

The object of the present invention is a bone joining plate which is suitable for securing the fractured bones even when the screwing alone is insufficient and which is easily adaptable to the conditions of application before or during the operation. According to the invention, a bone joining plate is provided having an oblong plate curved according to the bone surface, where at least two holes are arranged along the longitudinal axis and at least three pointed claws bent from the material of the plate are arranged at one of its ends. One of the claws is arranged suitably in the direction of the longitudinal axis of the plate and at least one further claw is perpendicularly arranged on each side of the plate. The holes may be circular or oval shaped, the latter one allows the eccentric arrangement of screws, whereby compression may be applied to the fractured surfaces. The bone joining plate according to the invention can be produced with claws laying in the plane, or tangent-plane of the plate, but the claws may also be bent from the plane of the plate, which makes their further shaping unnecessary.

4 Claims, 7 Drawing Figures

FIG. 3
FIG. 4
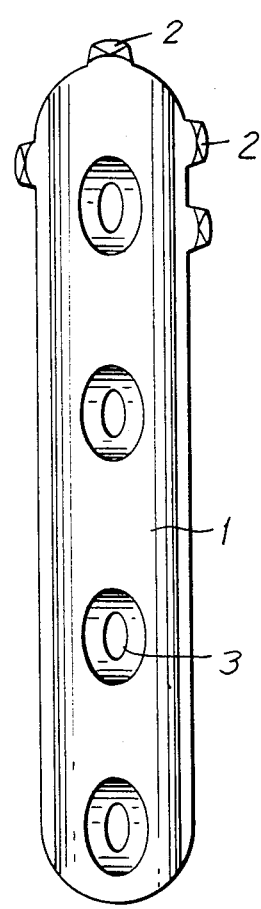
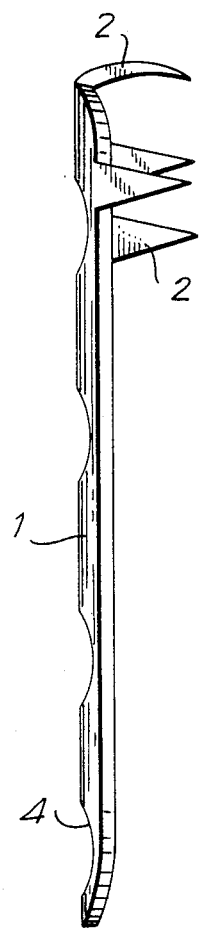

BONE JOINING PLATE

This is a continuation of application Ser. No. 610,639, filed May 16, 1984, now abandoned.

BACKGROUND OF THE INVENTION

The invention relates to a bone joining plate for securing the bone pieces of a bone fracture.

Joining plates are already used in case of fracture of the bones, e.g. the ankle or the wrist.

The purpose of such osteosynthesis with plate is the stable immobilization of the broken bone-ends in the proper position. This can only be achieved if the plate securing screws are fixed in the bone in sufficient quantity and in adequate quality. In case of fractures of the limbs generally sufficient room is available at both fractured ends for putting on the plate, the cortex ensures the safe anchorage of the screws. However in case of near-joint fractures, or those penetrating the joint, the bony substance is spongy, the cortex is thin and soft, the fractured end near the surface of the joint is frequently fragmentary and small. Thus in this case securing of the plate with screws is hardly possible: their anchorage in the soft and small pieces is inadequate. Under such conditions not even an adaptation synthesis can successfully be performed.

Similar problems appear in case of—mainly old—patients, whose bone structure is loose and more atrophied than the average. The metal screws do not become properly fixed in the thin, spongy bone, consequently the metal plate can not be satisfactorily secured with the screws, especially when in case of fragmentary fracture some of the line of breaks are at the spot of one or another screw. Such screws have no fixing effect.

The object of the present invention is a bone joining plate which is suitable for securing the fractured bones even when the screwing alone is insufficient and which is easily adaptable to the conditions of application before or during the operation.

According to the invention, a bone joining plate is provided having an oblong plate curved according to the bone surface, where at least two holes are arranged along the longitudinal axis and at least three pointed claws bent from the material of the plate are arranged at one of its ends. One of the claws is arranged suitably in the direction of the longitudinal axis of the plate and at least one further claw is perpendicularly arranged on each side of the plate.

The holes may be circular or oval shaped, the latter one allows the excentric arrangement of screws, whereby compression may be applied to the fractured surfaces.

The bone joining plate according to the invention can be produced with claws laying in the plane, or tangent-plane of the plate, but the claws may also be bent from the plane of the plate, which makes their further shaping unnecessary.

By securing of the plate the claws formed at one end can be bent to any optional plane with the use of pliers, and by hammering them into the bony substance, the anchorage of the plate-end is maximally ensured. The screws driven through the holes between the claws protect against slip-out. The superfluous claws which are not needed for anchorage are removed with nippers. The other holes of the plate can be used partly or fully for anchorage on the other fractured end. The plates can be produced in different lengths and with different number of holes for handling the various fractures. They are well applicable for example for the following:

securing the near-joint or joint fracture at the distant end of the radius;

securing the fragmentary near-joint or joint fracture at the near-end of the ulna;

securing the fractures of the outer ankle/the profile of this alternative is bent in advance conforming to the anatomical shape of the ankle appendix/;

securing the near-joint fracture or the one penetrating the joint at the distant end of the tibia;

securing the fragmentary, near-joint or joint fractures of the upper arm bone, or securing the femur and the tibia during the axial readjustment near the knee.

Further details of the invention are described by way of examples with the aid of drawings, in which:

BRIEF DESCRIPTION OF THE DRAWINGS

FIG. 3 is a front view of an alternative bone joining plate,

FIG. 4 is a side view of the bone joining plate shown in FIG. 3,

DETAILED DESCRIPTION OF THE DRAWINGS

Figure 1:
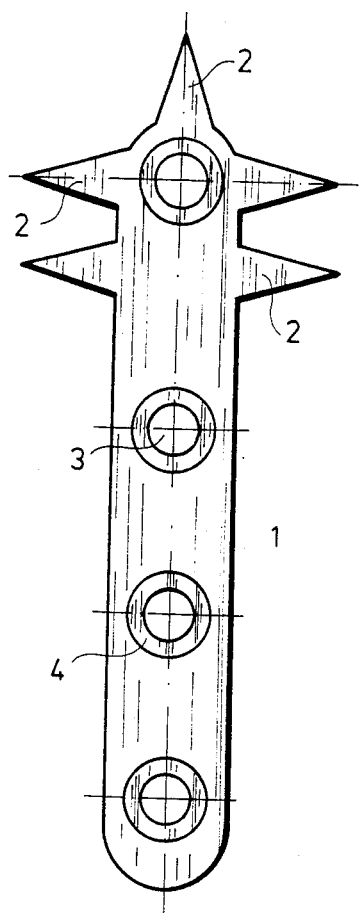
FIG. 1 is a front view of the bone joining plate according to the invention.
Figure 2:
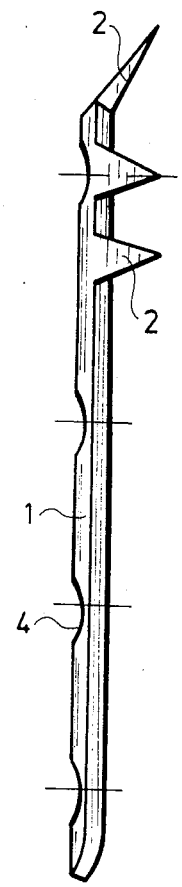
FIG. 2 is a side view of the bone joining plate shown in FIG. 1.

The method shown in FIGS. 1 and 2 according to the invention is the most generally used alternative of the bone joining plate. One end of the plate 1 is provided with claws 2 and holes 3 arranged along the longitudinal axis. The holes 3 are recessed 4 in order to level the screws with the surface of the plate 1.

As shown in the diagrams, plate 1 is slightly curved to fit easily to the surfaces of the bone.

Claws 2 are formed from the material of the plate 1 and they lie along the plane, or—since they are curved plates—along the tangent-plane.

The claws 2 are pointed and sharp to be hammered easily into the bone.

Another possible alternative of the bone joining plate according to the invention is shown in FIGS. 3 and 4. The plate 1 is similar to the one shown in FIGS. 1 and 2, but the claws 2 are curved and bent inwards from the plane of the plate 1.

In this way, bending of the claws 2 is unnecessary during operation, and thus its fast implantation is possible.

Further difference is that holes 3 are oval, instead of circular cross section, and similarly recesses 4 too are of such shape. This allows the use of screws in 'excentric positions.

The bone joining plate may be used as follows.

The bone surface is exposed with the conventional surgical technique, then the broken bone parts are set and temporarily secured. Thereafter the suitably selected and, if needed, bent bone joining plate is placed on the broken bone and the teeth are pressed into the bone with the finger, or by light hammering. Then the end of the bone joining plate opposite the teeth is fixed to the part of the bone near the body and screws are driven in between the teeth and those fitting into the holes.

If the fracture is fragmentary, then the broken pieces are first temporarily secured to each other by stitching wire, then—if needed—a drag-screw is inserted and finally the bone joining plate according to the invention is applied for compensation of the forces.

The advantage of the bone joining plate according to the invention is that the surgical treatment of fractures involving dislocation is simplified in most cases. It can be used even when the applicability of the conventional methods is limited or excluded because of the fragmentary bone fracture. Furthermore, it provides opportunity for the use of bone screws compressing the broken bone surfaces to each other in case of oblique line of break.

Use of the bone joining plate according to the invention allows a firm jointing of the broken bone parts without external fixing. If such would be required, it is justified by the dislocation during healing of the injured ligaments, and this determines the time of plaster wearing as well.

Use of the bone joining plate according to the invention is shown in detail by way of examples.

EXAMPLE 1

Figure 5:
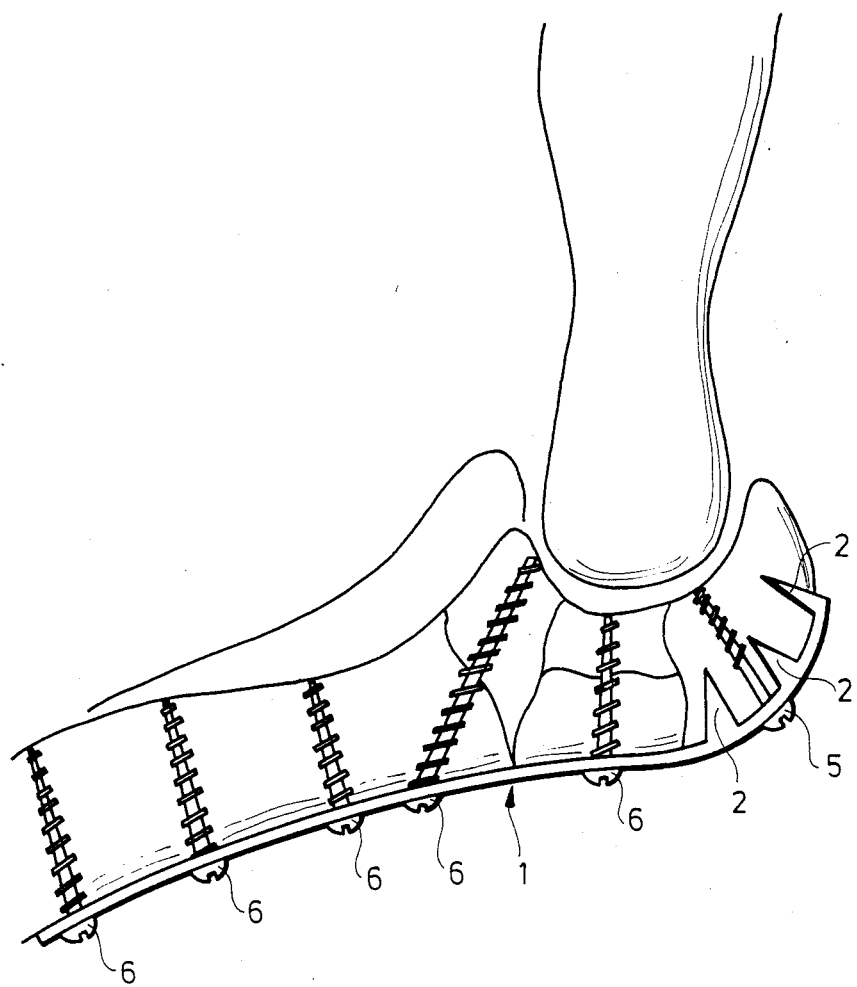
FIG. 5 shows the use of the bone joining plate built in for securing an elbow fracture.

FIG. 5 illustrates a fragmentary elbow fracture extending to the joint surface, which is situated at the end near the ulna.

After exposure the haematoma is removed from the joint, then the irregularities of the joint surface are eliminated by resetting the dislocated pieces. If necessary, the dislocated pieces are supported by a spongy part taken off the hip bone.

Thereafter, the bone joining plate shown in FIGS. 1 and 2 is bent so that the pieces temporarily secured with stitching wires are embraced by the claws 2, and the bent ends are finally secured in the bony substance.

A drag-screw 5 is inserted into the hole 3 between the claws 2 after preliminary drilling and thread cutting. The drag-screw 5 is driven in as to have the threaded part fixed in the elbow tip.

Cortical screw 6 are driven into the other holes 3 and this way the plate 1 is secured to the cortex.

EXAMPLE 2

Figure 6:
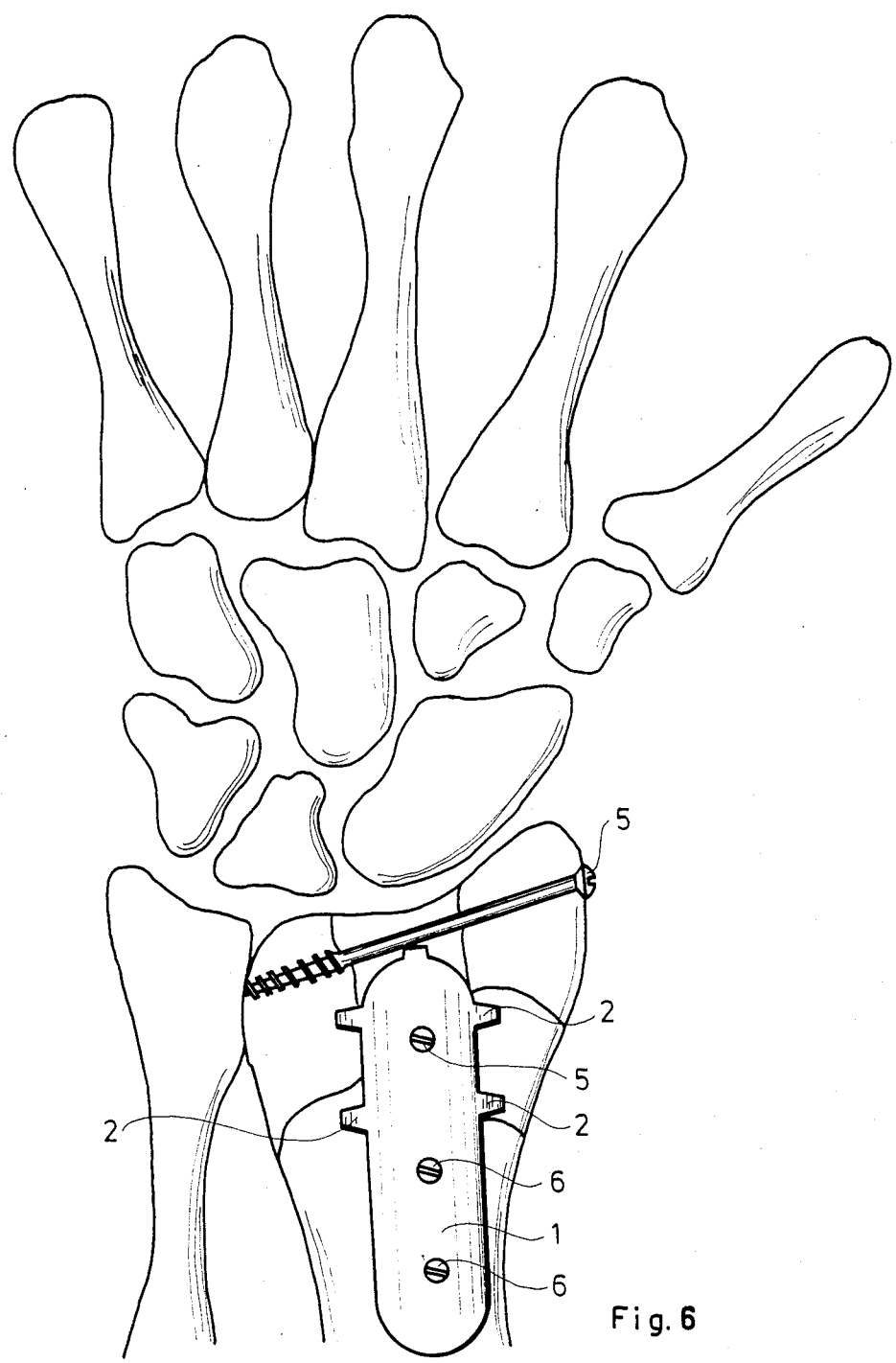
FIG. 6 is an example for securing a wrist fracture and FIG. 7 is a bone joining plate used in case of fractured outer or inner ankle.

FIG. 6 shows a fragmentary fracture of the wrist penetrating the joint at the distant end of the radius.

Prior to application of the bone joining plate according to the invention the joint and the slipped-in pieces are set into their original position. The set bone pieces are temporarily secured with stitching wires, then such bone joining plate is placed over the injured part which is shaped by the suitable bending of the claws 2 so that each claw 2 secures a broken piece, at the same time the end of plate 1 supports the zone of injury. The claws 2 are hammered into the spongy bone substance. In some cases a locus is prepared first for the claws with scalping iron matching the profile of the claws 2.

Thereafter a drag-screw 5 is driven into the hole 3 between the claws 2, while small cortical screws 6 are driven into the other holes 3. This way the broken pieces are secured in the proper position.

EXAMPLE 3

Figure 7:
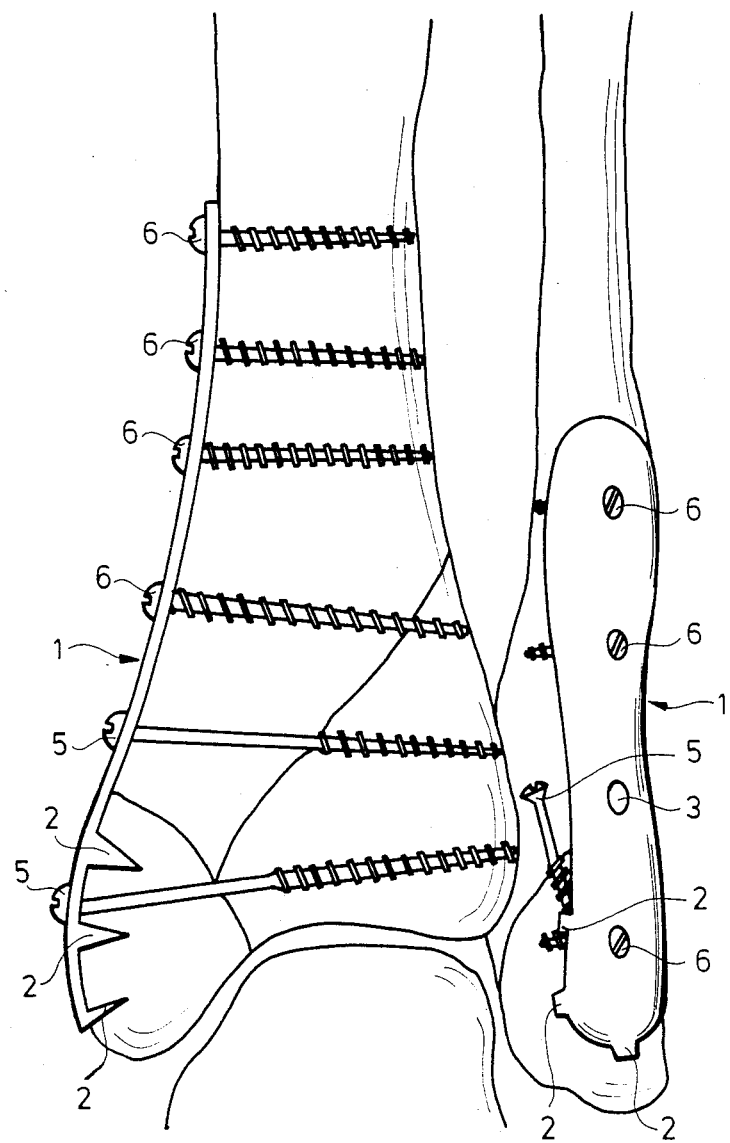

Fragmentary fracture of the inner ankle penetrating the joint at the distant end of the tibia is shown on the left side of FIG. 7.

Following the exposure, the haemotoma is removed from the joint. The irregularities of the joint surface are eliminated by resetting the broken pieces, and the pieces are temporarily secured with stitching wire. If necessary, the pieces are supported with a spongy bone part removed from the femur.

The set position is secured with the bone joining plate according to the invention. The claws 2 of plate 1 shown in FIGS. 1 and 2 are bent with pliers so that the plate embraces the region of the inner ankle and the claws 2 are secured in the spongy bony substance.

Thereafter, a drag-screw 5 is driven into the hole 3 between the claws 2. Similar drag-screw 5 is driven into the next hole 3 too after preliminary drilling and thread cutting.

Small cortical screws 6 are then inserted into the further holes 3 of the plate 1.

EXAMPLE 4

A fracture of the outer ankle is also shown in FIG. 7 which is a longitudinal spiral fracture with broken sphenoid.

Following the exposure, the haematoma is removed from the fracture and the periosteum is separated from the broken pieces to such extent as to reset the two main pieces without obstruction.

Thereafter a drag-screw 5 is inserted in the front and backwards and, if necessary, the broken piece or pieces are secured in their position with separate drag-screws or stitching wires. Next, the bone joining plate shown in FIGS. 3 and 4 is placed on the outer surface of the bone in such a way that the claws bent in advance are pressed into the distant piece, or hammed with upsetting device into the spongy bony substance. Small cortical screws 6 are driven into the holes 3 between the claws 2 after preliminary drilling and thread cutting, then moving towards the head small cortical screws 6 are driven into the near-by piece after drilling and thread cutting. Since the second hole 3 from the claws 2 falls above the gap of the fracture, this hole is not used.

The examples show that the bone joining plate according to the invention can be used in an extremely wide range of the bone fractures, its adaptation to the given fracture is very simple and the anchorage is safe.

Though only some alternatives of the bone joining plate according to the invention were shown in the drawing and examples, it is obvious that it can be realized in many other alternatives as well.

What we claim is:

1. Bone joining plate characterized in that it comprises an oblong plate curved inwardly along a longitudinal axis, and having at least two bone-joining, screw-holding holes arranged along said longitudinal axis of said plate and at least three pointed claws formed from the material of the plate at only one of its ends, said claws being arranged such that a first claw lies in said longitudinal axis and said remaining claws are arranged such that at least one, on each side of said first claw, lies along a line perpendicular to said longitudinal axis.

2. Bone joining plate as claimed in claim 1, characterized in that one of the claws /2/ is arranged in the direction of the longitudinal axis of the plate /1/ and further claws /2/ perpendicular to the plate are arranged on both sides of the plate /1/.

3. Bone joining plate as claimed in claim 1, characterized in that said claws are bent down from the curved plane of the plate.

4. A new bone joining plate as claimed in claim 1, wherein said screw holding holes are recessed.

* * * * *